US00PP17059P3

(12) United States Plant Patent
Solano

(10) Patent No.: US PP17,059 P3
(45) Date of Patent: Aug. 22, 2006

(54) ***COLEUS* PLANT NAMED 'BALAUBLACH'**

(50) Latin Name: *Solenostemon scutellarioides*
Varietal Denomination: Balaublach

(75) Inventor: Rolando Solano, Dulce Nombre de Cartago (CR)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/017,552

(22) Filed: Dec. 20, 2004

(65) Prior Publication Data

US 2006/0137066 P1 Jun. 22, 2006

(51) Int. Cl.
*A01H 5/00* (2006.01)

(52) U.S. Cl. ..... Plt./373

(58) Field of Classification Search ..... Plt./373
See application file for complete search history.

*Primary Examiner*—Anne Marie Grunberg
*Assistant Examiner*—Louanne Krawczewicz Myers
(74) *Attorney, Agent, or Firm*—Wood, Phillips, Katz, Clark & Mortimer

(57) ABSTRACT

A new and distinct cultivar of *Coleus* plant named 'Balaublach', characterized by variegated foliage of varying amounts of green and grayed-purple, and vigorous, upright bushy growth habit.

1 Drawing Sheet

Latin name of genus and species of plant claimed: *Solenostemon scutellarioides.*
Variety denomination: 'Balaublach'.

BACKGROUND OF THE INVENTION

The present invention relates to a new and distinct cultivar of *Coleus* plant botanically known as *Solenostemon scutellarioides* and hereinafter referred to by the cultivar name 'Balaublach'.

The new cultivar originated in a controlled breeding program carried out during January 2002 at Cartago, Costa Rica. The objective of the breeding program was the development of new *Coleus* cultivars with unique leaf shapes and coloration.

The female (seed) parent of the new *Coleus* was the *Solenostemon scutellarioides* variety 'Ducksfoot', not patented. The male (pollen) parent of the new variety was proprietary breeding selection 01Co8, not patented. The new cultivar was discovered and selected by the inventor as a single plant within the progeny of the above stated cross-pollination during August 2002.

Asexual reproduction of the new cultivar, by terminal stem cuttings since 2002 in West Chicago, Ill., has demonstrated that the new cultivar reproduces true to type with all the characteristics, as herein described, firmly fixed and retained through successive generations of such asexual propagation.

SUMMARY OF THE INVENTION

The following characteristics of the new cultivar have been repeatedly observed and can be used to distinguish 'Balaublach' as a new and distinct cultivar of *Coleus* plant:

1. Variegated foliage of varying amounts of green and grayed-purple color.
2. Upright bushy form.
3. Vigorous growth habit.

Plants of the new cultivar differ from plants of the female parent primarily in foliage shape and color and from the male parent primarily in foliage color.

Of the *Coleus* cultivars known to the inventor, the most similar to the new cultivar is 'Balaustop', not patented. However, in side by side comparisons, plants of the new cultivar differ from plants of 'Balaustop' in the following characteristics:

1. Plants of the new cultivar have longer internodes than plants of 'Balaustop'.
2. Plants of the new cultivar have more red color in the foliage than plants of 'Balaustop'.

BRIEF DESCRIPTION OF THE PHOTOGRAPHS

The accompanying photographs show, as nearly true as it is reasonably possible to make the same in color illustrations of this type, a typical plant of the new cultivar. Colors in the photographs differ slightly from the color values cited in the detailed description, which accurately describe the colors of 'Balaublach'. The plant was grown for 7 weeks in a greenhouse at West Chicago, Ill.

DETAILED BOTANICAL DESCRIPTION

Figure 1:
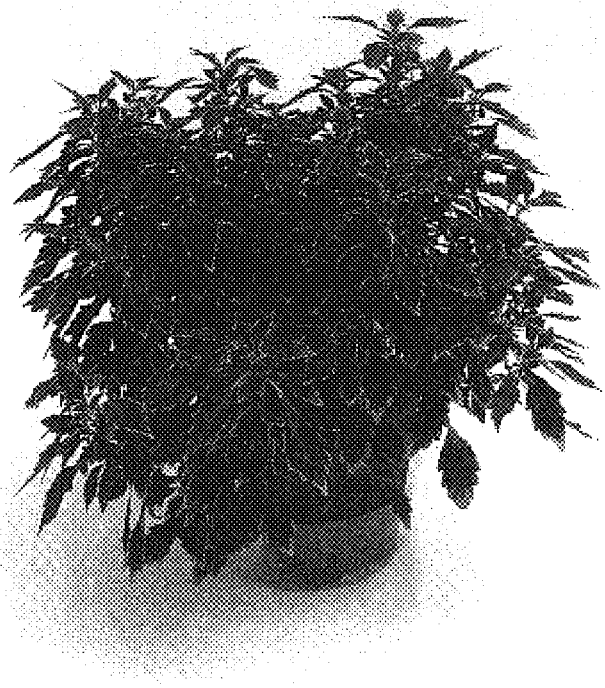
FIG. 1 illustrates a side view of the overall growth habit of 'Balaublach'.
Figure 2:
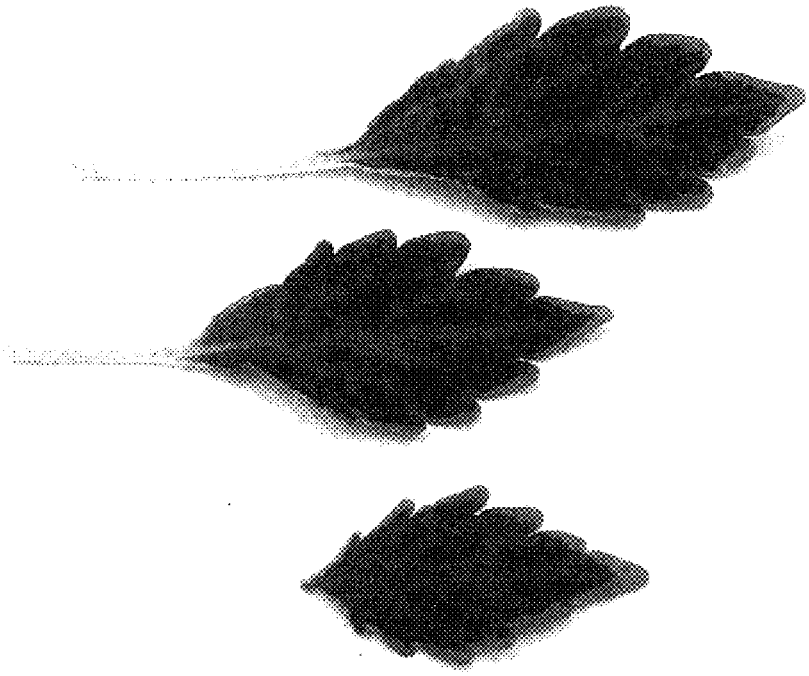
FIG. 2 illustrates a close-up view of a single leaf of 'Balaublach'.

The new cultivar has not been observed under all possible environmental conditions to date. Accordingly, it is possible that the phenotype may vary somewhat with variations in the environment, such as temperature, light intensity, and day length without, however, any variance in genotype.

The chart used in the identification of colors described herein is The R.H.S. Colour Chart of The Royal Horticultural Society, London, England, 2001 edition, except where color terms of ordinary significance are used. The color values were determined on Sep. 24, 2004 in West Chicago, Ill., between 10:00 and 11:45 a.m. under natural light conditions.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 7 weeks while utilizing a soilless growth medium. Greenhouse temperatures were maintained at approximately 75° to 85° F. (24° to 29° C.) during the day and approximately 60° to 70° F. (15° to 21° C.) during the night. Greenhouse light levels were maintained at approximately 4,000 to 10,000 footcandles during the day.

Classification:

*Botanical.*—*Solenostemon scutellarioides* cultivar 'Balaublach'.

Parentage:

*Female (seed) parent.*—'Ducksfoot', not patented.

*Male (pollen) parent.*—Proprietary breeding selection 01Co8, not patented.

Propagation:

*Type cutting.*—Terminal tip.

*Time to initiate roots.*—Approximately 4 to 6 days.

*Time to produce a rooted cutting.*—Approximately 14 to 21 days.

*Rooting habit.*—Freely branching.

*Root description.*—Fine, fibrous.

Plant description:

*Growth habit.*—Vigorous and freely branching.

*Form.*—Upright, bushy.

*Crop time.*—Five to seven weeks are required to produce mature plant from rooted cuttings.

*Size.*—Height from soil level to top of foliage: Approximately 23.4 cm. Width (area of spread): Approximately 37.5 cm.

Branch description — Quantity: Approximately 6 per plant. Strength: Strong. Shape: Square in cross section. Length: Approximately 20.5 cm. Diameter: Approximately 6 mm. Texture: Pubescent. Color: 144A. Length of center internode: Approximately 3.7 cm.

Foliage description:

*Number of leaves per branch.*—Approximately 19.

*Fragrance.*—Slight, spicy.

*Form.*—Simple.

*Arrangement.*—Opposite.

*Aspect.*—At right angle to stem.

*Shape.*—Ovate.

*Margin.*—Lobed.

*Apex.*—Acute.

*Base.*—Attenuate.

*Venation pattern.*—Pinnate.

*Size of mature leaves.*—Length: Approximately 5 cm. Width: Approximately 2.6 cm.

*Texture.*—Upper surface has moderate pubescence. Lower surface has sparse pubescence with moderate pubescence along veins.

*Color of young and mature foliage.*—Upper surface: Venation: 185A. Margin: 146A. Area along veins and mid-vein: 185B. Between veins: 138B.

*Color of young and mature foliage.*—Lower surface: Venation: 154D. Margin: 146C. In center, on either side of mid-vein and veins: 187A.

*Petiole.*—Length: 2.9 cm. Diameter: 1.5 mm. Texture of upper surface: Sparsely pubescent. Texture of lower surface: Moderately pubescent. Color of upper and lower surface: 154D.

Flower description:

*Type and habit.*—Single, zygomorphic, bilabiate flowers arranged in verticillasters on terminal spikes.

*Flowering season.*—'Balaupea' produces flowers in late spring.

*Lastingness of bloom on the plant.*—Approximately 3 to 4 days.

*Fragrance.*—None.

*Spike.*—Length: 8 cm. Diameter: Approximately 2.8 cm. Approximately 11 verticillasters per spike. Quantity of open flowers per verticillaster: 2–5.

*Flower bud.*—Shape: Oblate. Length: Approximately 4 mm. Diameter: Approximately 2 mm. Color: Closest to 76A.

*Corolla.*—Diameter: 4 mm. Length: 1.1 cm. Petal arrangement: 5 petals, 1 upper petal forming banner, 4 lower petals fused to form keel. All 5 petals fused at base to form tube. Banner — Length: 7 mm. Width: 2 mm. Apex: Rounded. Margin: Entire. Texture of upper surface: Glabrous. Texture of lower surface: Pubescent. Color of upper surface: N89D. Color of lower surface: Closest to N86D. Keel — Length: 3 mm. Width: 4 mm. Apex: Rounded. Margin: Entire. Color of upper surface: N82D at apex, N155A at base. Color of lower surface: Closest to 76A at apex, 155A at base.

*Calyx.*—1 calyx tube per flower, formed by 5 fused sepals. Length: 3 mm. Diameter: 2 mm. Apex: Acute. Texture of upper surface: Glabrous. Texture of lower surface: Pubescent. Color of upper and lower surface of sepal: 144B with overlay of 183A at tip.

*Pedicels.*—Strength: Moderate. Angle: Acute. Length: Approximately 4 mm. Diameter: Approximately 0.5 mm. Texture: Densely pubescent. Color: 144C.

*Reproductive organs.*—Androecium: 4 stamens. Anther shape: Oval. Anther length: Approximately 0.5 mm. Anther color: N92B. Pollen amount: None observed. Gynoecium: Pistil quantity: 1 per flower. Pistil length: 8 mm. Stigma shape: 2 parted. Stigma length: Approximately 0.5 mm. Style length: Approximately 6.5 mm. Style color: 155D. Ovary length: Approximately 1 mm. Ovary color: 150D.

Seed and fruit production: Neither seed nor fruit production has been observed.

Disease and pest resistance: Resistance to diseases and pests common to *Coleus* has not been observed.

What is claimed is:

1. A new and distinct cultivar of *Coleus* plant named 'Balaublach', substantially as herein shown and described.

* * * * *